United States Patent [19]
Frenzel

[11] Patent Number: 4,491,634
[45] Date of Patent: * Jan. 1, 1985

[54] CHEMILUMINESCENT IMMUNOASSAY WITH ACTIVATOR OF HYDROGEN PEROXIDE AND A CHLORAMINE

[76] Inventor: Bernd Frenzel, Spitzelbergstrasse 18a, D-8000 Munich 71, Fed. Rep. of Germany

[*] Notice: The portion of the term of this patent subsequent to Feb. 21, 2001 has been disclaimed.

[21] Appl. No.: 333,407

[22] Filed: Dec. 22, 1981

Related U.S. Application Data

[63] Continuation-in-part of Ser. No. 267,414, May 26, 1981, Pat. No. 4,433,060.

[30] Foreign Application Priority Data

Dec. 22, 1980 [DE] Fed. Rep. of Germany ....... 3048447
Feb. 20, 1981 [DE] Fed. Rep. of Germany ....... 3106444
Aug. 10, 1981 [DE] Fed. Rep. of Germany ....... 3131615
Nov. 2, 1981 [DE] Fed. Rep. of Germany ....... 3143423

[51] Int. Cl.$^3$ ..................... G01N 33/54; G01N 33/58; G01N 33/52
[52] U.S. Cl. ................................... 436/518; 436/536; 436/546; 436/800; 436/820
[58] Field of Search .................. 23/230 A; 424/8, 12; 436/518, 536, 546, 800, 820

[56] References Cited

U.S. PATENT DOCUMENTS 4,104,029 8/1978 Maier ................................. 23/230 B
4,193,983 3/1980 Ullman et al. ....................... 436/528
4,238,195 12/1980 Boguslaski ......................... 23/230 B

*Primary Examiner*—Sidney Marantz
*Attorney, Agent, or Firm*—Oblon, Fisher, Spivak, McClelland & Maier

[57] ABSTRACT

In a process for qualitative and quantitative determination of antigens, antibodies, and antigen/antibody complexes, using a chemiluminescent marker in a liquid-phase or solid-phase assay the combination of chemiluminescent marker and activator for the marker is selected from the combinations (a) $H_2O_2$/chloramine (or functionally equivalent derivative) - fluorescein, methylene blue, thionine or functionally equivalent derivatives of these chemiluminescent markers; and (b) calcium hypochlorite-fluorescein or functionally equivalent derivative.

The method is simpler and more sensitive than known methods and presents less danger to those performing the assay.

8 Claims, 1 Drawing Figure

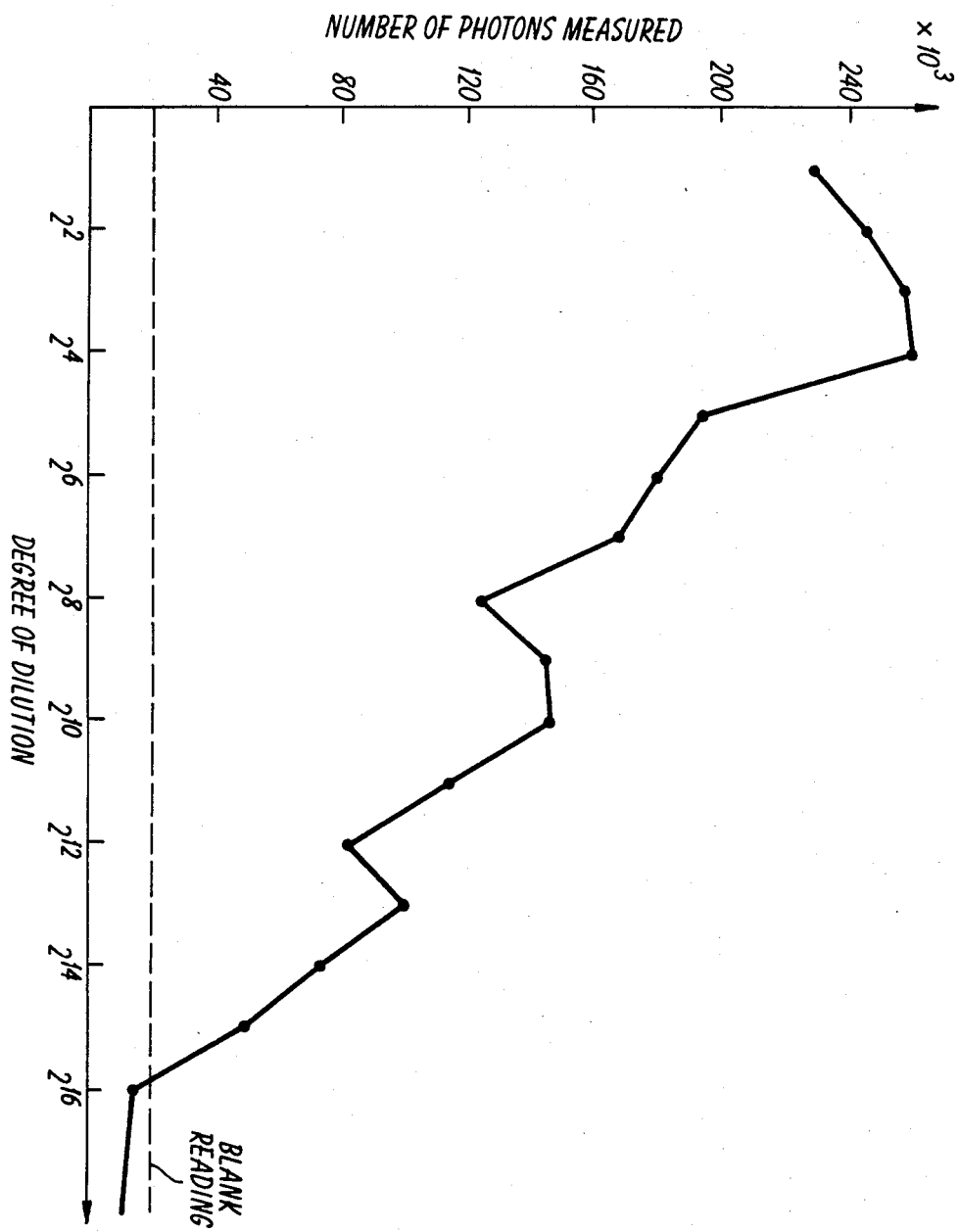

CHEMILUMINESCENT IMMUNOASSAY WITH ACTIVATOR OF HYDROGEN PEROXIDE AND A CHLORAMINE

RELATED APPLICATION

This application is a continuation-in-part of Applicant's copending application Ser. No. 267,414, filed May 26, 1981, U.S. Pat. No. 4,433,060.

BACKGROUND OF THE INVENTION

1. Field of the Invention

This invention relates to a method for determining antigens, antibodies and their complexes, qualitatively and quantitatively, and more particularly to a method for determining such substances which uses a chemiluminescent marker and an activator in a conventional heterogeneous assay.

2. Description of the Prior Art

The quantitative determination of antigens, antibodies and their complexes in secretions, excreta and body fluids of vertebrates and humans is of great importance in biology and medicine. These procedures can be of great utility in diagnosis, as well as for other applications.

It is known to detect an immunological reaction by marking one or more of the ligands with a radioactive isotope, or by conjugating it with an enzyme, a fluorescent dye or a chemiluminescent material such as luminol or luciferin.

Radioimmunoassay is disclosed in Journal of Clinical Endocrinology 27 (1967) p. 973 and Ibid. 28 (1968) p. 343. The essential disadvantage of this technique lies in the necessity of working with isotopes which emit radiation and in the necessarily expensive equipment needed to carry out such assays.

Marking a reaction component with an enzyme has the disadvantage that marking is complicated and the final reaction product is difficult to preserve and use. Furthermore, the enzymes used are biologically active substances of extremely complex nature, which is the basis for these difficulties. Finally, the substrates which are used in the ultimate determination of the bound enzymes are carcinogenic, which is evidently disadvantageous. The enzyme assay of this type is discussed in Bull. World Health Organ. 53 (1976).

In the fluorescence technique, the reaction products containing antigens and antibodies are detected by irradiation with light of short wavelength. In this case, the exciting light must be distinguished from the emitted light, which requires very expensive apparatus.

The chemiluminescent materials hitherto prepared for chemiluminescence investigation have been very difficult to bind to a ligand used in an immunological reaction, and, furthermore, up to 99.3% of the original luminescence is lost when the compounds are bound. This is disclosed in, e.g., Nature, Vol. 299 (1979), pp. 646–647. It is further reported in Journal of Immunological Methods 21, pp. 178–184, that the chemiluminescent material luminol is unsuitable for routine clinical laboratory tests for this reason.

The disclosures of U.S. Pat. No. 4,193,983 are to the contrary. In that patent, luminol is plainly disclosed to be a compound especially suited for this purpose. Hydrogen peroxide or calcium hypochlorite are mentioned as activators for chemiluminescence. Furthermore, in this U.S. Pat. No. the use of fluorescein isothiocyanate is disclosed for a homogeneous fluorescence assay.

In spite of intensive effort, it has hitherto been impossible to carry out a process of the type described above with satisfactory cost and efficiency. This is also true, for example, for the assay described in U.S. Pat. No. 4,238,195. In that patent, markers in the form of fluorescein and its derivatives were proposed, which require especially energy-rich materials for activation. These materials are prepared by a very complex reaction between derivatives of oxalic acid (oxalyl chlorides among others) and hydrogen peroxide, and their preparation requires a great expenditure of labor. Furthermore, it is not inconceivable that under certain conditions these materials might generate poisonous phosgene.

Hence, a need has continued to exist for a chemiluminescent marker for immunological reactions which avoids the drawbacks of the known materials.

SUMMARY OF THE INVENTION

Accordingly, it is an object of this invention to provide a chemiluminescent marker-activator system which is simple to prepare and use.

A further object is to provide a chemiluminescent marker-activator system which is not dangerous to use.

A further object is to provide a chemiluminescent marker-activator system which has a high sensitivity.

A further object is to provide a chemiluminescent marker-activator system which is relatively inexpensive.

Further objects of the invention will become apparent from the description of the invention which follows.

It has now been found that these objects of the invention can be achieved by using a combination of activator and chemiluminescent dye marker selected from the following combinations of activator and chemiluminescent marker:

(a) $H_2O_2$/chloramine (or functionally equivalent derivatives thereof)-fluorescein, methylene blue or thionine (or functionally equivalent derivatives of these dyes), and (b) calcium hypochlorite-fluorescein (or functionally equivalent derivatives).

BRIEF DESCRIPTION OF THE DRAWING

The sole FIGURE is a graph of the number of photons emitted versus the dilution of the test solutions in the chemiluminescent analysis of Example 3.

DETAILED DESCRIPTION OF THE INVENTION AND PREFERRED EMBODIMENTS

In the context of the description of the invention in this application the concepts antigen and antibody should be given their broadest meaning. Antigen means a material which, when it is introduced into the organism, whether human or other animal, provokes the formation of antibodies. Antigens include foreign proteins of animal and vegetable origin, especially those of infectious organisms, as well as many materials of complex constitution having structures of the lipid, saccharide (or sugar), amine and azo types. These include substances such as conjugated proteins, proteins, polysaccharides, lipids or nucleic acids, which in the vertebrate or human organism provoke the formation of antibodies and react specifically with them. Haptens in general also should be included, which are also called "incomplete antigens". Because of their small size they cannot by themselves provoke the formation of antibodies, but they can enter into a specific binding with the corresponding antibody. Viruses, bacteria, fungi, or parts thereof, for example, can be antigens. Furthermore, other materials, e.g., certain hormones, vitamins, enzymes, or medicaments, can be included in the concept "antigen". The definition of the concepts "antigen" and "antibody" is discussed in Kabat, "Einführung in die Immunochemie und Immunologie", Springer Verlag, 1971, pp. 9–25 and 143–197.

Antibodies in the context of this invention are specific products of the immune response, which are formed in vertebrate and human organisms after challenge with antigen, and can react specifically with the antigen. Besides antibodies, certain binding proteins should be expressly mentioned which can bind specifically to one or more materials, such as antibodies. An example of these is found in Protein A. Especially important are the antibodies which can be classified as immunoglobulins of the classes IgG, IgM, IgA and IgE. These are described in detail in Kabat, "Einfte,uml/u/ hrung in die Immunochemie und Immunologie," Springer Verlag, 1971, pp. 143–197.

The process of the invention is especially important for detecting and identifying antigens and antibodies in viral and bacterial diseases. Among these, the determination of the surface antigens of hepatitis-B virus is of special significance. The determination of antibodies against herpesvirus and togavirus also can be performed with special advantage.

Experience with fluorescein and fluorescein derivatives has shown that they are especially good for binding to proteins and conjugated proteins. The derivatives are those in which fluorescein is substituted with one or more groups that facilitate its coupling with the abovementioned antigens and antibodies. Among these, isothiocyanate and isocyanate groups have proved to be especially advantageous as substituents which mediate and facilitate coupling. An especially preferred position for the isocyanate group is illustrated in the following formula (FITC):

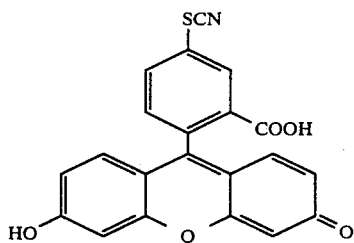

Besides the substituents which mediate and facilitate coupling, the fluorescein derivatives may also optionally be provided with substituents which do not enter into coupling reactions. The coupling ability of the fluorescein or derivatives can be promoted and improved by adding a suitable reagent which produces a coupling reaction or a bridging reaction between the basic fluorescein molecule and the antigen, antibody or equivalent.

The advantage in the use of methylene blue lies in the fact that, especially in basic media, no additional coupling group is required for coupling with antigens, antibodies, or their complexes.

When thionine is used as a marker, a coupling group must be introduced. The coupling groups correspond to those disclosed for fluorescein. In practice, the carbodiimide derivative has proved to be especially suitable, especially (N-ethyl-N'-(3-methylaminopropyl)carbodiimide hydrochloride.

When "coupling ability" is mentioned in the context of this invention, this term should also be understood in the broadest sense. In no case is it intended to be expressly restricted to a very specific type of binding. Rather, it should merely be taken as expressing the concept that a binding or bound complex-type structure is formed by interaction between the marker and the ligand of the immunological reaction.

In particular cases, it is conceivable that the antigen to be marked cannot react with the selected chemiluminescent marker used or at least not to a sufficient extent. In such cases, the practitioner may make use of a conventional protein or conjugated protein which is first bound to the antigen, so that subsequently the marker can be bound to the protein portion of the resulting reaction product. The procedure can also be reversed, in which case the marker is first bound to the protein or conjugated protein and this chemiluminescent conjugate is caused to react with the antigen in question. Finally, it has been shown that the sensitivity of these assays can be very noticeably increased if, in the preparation of the chemiluminescent conjugate, the chemiluminescent marker in the form of fluorescein or its derivatives is bound to a protein, in particular, an immunoglobulin.

According to the principle of the invention, the chemiluminescent activator reacts with the chemiluminescent marker bound to the antigen, antibody or complex in such a way that the marker emits a photon.

For the chemiluminescent markers used in this invention, the combination of hydrogen peroxide and chloramine or its derivatives has proved to be especially well suited. It is surprising that hydrogen peroxide, which in the literature is frequently disclosed by itself as a single activator, is not suitable for use in this invention when used alone. The same thing is true for chloramine and its derivatives when they are used alone. It must be considered highly surprising that the combination of these two reagents produces an especially favorable solution of the problem addressed by the invention. Among the chloramines, chloramine T is preferred. Chloramine T is the internationally accepted generic name for N-chloro-4-toluenesulfonic acid amide, sodium salt, or sodium tosylchloramide. It is a very stable substance, which, like calcium hypochlorite, guarantees good reproducibility of each assay. The amount of chloramine (or derivatives) used is correlated in each case with the amount of hydrogen peroxide. Accordingly, the concentration of hydrogen peroxide which is chosen plays a part. It has been discovered that, with the following concentrations, superior results are attainable when equal volumes of solutions of each reagent are combined: a 0.5 to 30% by volume solution of hydrogen peroxide and a 0.1 to 8% by weight solution of chloramine T. In each case the practitioner can determine the effective composition of the activator prepared from hydrogen peroxide and chloramine or its derivatives with an insignificant expenditure of effort and without inventive activity.

Calcium hypochlorite, which is used as an activator for applications involving fluorescein isocyanate, exhibits various considerable advantages, especially in aqueous solution. Thus, the assay can be reproduced with extraordinary precision. The exact concentration of activator for a particular case can immediately be set. Generally, a solution of about 0.1 to 20% by weight, preferably 0.2 to 10% by weight of calcium hypochlorite, provides advantageous results. Especially preferred is a solution of about 1.0 to 4.0% by weight, and a 2% by weight solution is especially good.

The method of the invention can, as already pointed out in the introduction, be carried out using the techniques of conventional heterogeneous assays. Many kinds of processes of this type have been disclosed in the literature. By way of example, U.S. Pat. No. 4,238,195 may be mentioned (see especially column 15, lines 7-11).

The process df the invention can consequently be practiced in many ways, as the practitioner will immediately recognize. First, as is axiomatic, the antigen/antibody complex is formed by an immunological reaction which is carried out by known procedures. This can be accomplished in various methods, in the first of which either the antigen or the antibody is present in solution, or one ligand, i. e., the antigen or antibody, is bound to a solid phase. Accordingly, the term liquid-phase assay or solid-phase assay is used. In either case, after the immunological reaction is complete, the antigen/antibody complex is separated from the residual reaction mixture. In the solid-phase assay this can be accomplished simply by decanting the supernatant liquid, after centrifuging if necessary. In the liquid-phase assay the separation is carried out by, for example, centrifuging followed by decantation or by filtering, especially by ultrafiltration, chromatography, and the like. The antigen/antibody complex isolated by the described process or by a similar procedure is finally contacted with a liquid medium which contains the chemiluminescent conjugate which reacts with the complex.

The chemiluminescent conjugate contains, besides the antigen or antibody (or protein), one of the previously enumerated markers. A new chemiluminescent complex is formed from the chemiluminescent conjugate and the antigen/antibody complex which is isolated by one or more of the described separation procedures. According to this procedure, the complex can be already present in the measuring cuvette, can be generated therein, or can be transferred into the cuvette. In each case, before the measurement is carried out, the activator is added. The type of solvent, insofar as one is required, is not important. It is preferred, however, that the activator be present in an aqueous medium, especially an alkaline one.

A procedure is outlined above in which the chemiluminescent marker is "indirectly" bound to the ligand in an immunological reaction. Besides that, however, a "direct" assay is also possible. In that case either an antigen or an antibody is introduced beforehand. Depending on the material introduced, an antibody conjugate or an antigen conjugate (with the chemiluminescent marker) is added and a chemiluminescent complex is formed which is subsequently isolated. Subsequently the chemiluminscence measurement is carried out by adding the activator.

The process of the invention can be carried our very advantageously as a sandwich assay. A sandwich assay can be carried out in principle as either a liquid-phase or a solid-phase assay. The essential characteristic of a chemiluminescent conjugate formed in the course of a sandwich assay lies in the fact that, in the complex whose chemiluminescence is measured, the ligand to be detected has reacted as an antigen or antibody with both the conjugated and non-conjugated forms of its complementary ligand. Disregarding the attached marker, a symmetrically constructed complex is present, in which the central ligand is the antigen or antibody to be determined. The complementary ligand or reagent introduced beforehand thereby interacts with the central ligand on both sides.

However, conventional competitive binding assays may also be included in the concept of the invention. In one reaction of this type a ligand of an immunological reaction is present in both marked and unmarked forms. Both these ligands interact with the complementary ligand. Thus, the first ligand can be an antigen (marked or unmarked). In that case the second ligand is an antibody. The marked first ligand and the second ligand (antigen or antibody) are quantitatively present. After the completion of the immunological reaction, either the unbound fraction of the marked first ligand or the complex formed is measured in the usual way by adding the activator. This technique is generally known (see U.S. Pat. No. 4,238,195), and, accordingly, its variations are familiar to one skilled in the art.

The chemiluminescence can be measured with commercially available photometers. A calibration curve can be determined by using predetermined known amounts of antigen and antibody. For an unknown substance (antigen or antibody) the measured value can then be quantitatively evaluated by applying the calibration curve.

Furthermore, it is also possible, provided it is understood as only semi-quantitative, to make a comparison of the sensitivity with that of other known assays. Radioimmunoassay, which hitherto has been regarded as especially sensitive, although encumbered with by the disadvantages outlined above, is, in the majority of applicable areas, far inferior in sensitivity to the process of this invention. Thus, for example, the antibody titer of a hyperimmune serum against bovine serum albumin, raised in the rabbit, was determined to be 1:4069 by radioimmunoassay, while by the process of this invention ($H_2O_2$/chloramine-FITC) a sensitivity of 1:32788 is attainable. Thus, the sensitivity is greater by a factor of almost 8. Other conventional assays were far less sensitive than the one compared above. Thus the following antibody titers were determined by known assays:

| | |
|---|---|
| by nephelometer | 1:16 |
| by immunodiffusion | 1:64 |
| by complement binding | 1:128 |
| by ELISA | 1:512 |

The advantages realizable by the process of the invention can be seen in that the chemiluminescent marker can be extraordinarily simply bound to a ligand of an immunological reaction, that is, in the form of an antigen, antibody or binding protein. Furthermore, the markers used in the process of the invention as well as the activators are simple to synthesize and unobjectionable as regards the personnel practicing the process of the invention, especially with respect to the liberation of poisonous compounds. The conjugates or complexes prepared in this assay are relatively stable, which is an advantage for the process of the invention.

The technical results attainable with the invention have to be considered as extraordinarily surprising. Thus, for example, fluorescein and its derivatives when bound to one of the ligands of an immunological reaction exhibit a significantly higher sensitivity than the corresponding compounds in the free state. The number of photons emitted by the luminescing conjugate or complex is some 1000 times greater than the number of photons emitted by the unbound substance. In this connection it is significant that in the Journal of Physical Chemistry, Vol. 78, No. 17, pp. 1681-1683 (1979) it is expressly remarked that to obtain a measurable photon yield a disproportionately large amount of fluorescein or fluorescein isothiocyanate has to be used. This has hitherto discouraged the technical community from using fluorescein or its derivatives in the practical application of carrying out immunological assays based on measuring chemiluminescence.

Having generally described the invention, a more complete understanding can be obtained by reference to certain specific examples, which are provided herein for purposes of illustration only and are not intended to be limiting unless otherwise specified.

EXAMPLE 1

Determination of the detection limit of pure fluorescein isothiocyanate (FITC) and determination of the detection limit of a FITC-conjugate In order to determine the detection limit of pure FITC, 1 mg FITC was dissolved in 10 ml of distilled water. Then the optical density of a 1:100 dilution was measured at 495 nm by a photometer. Ten more dilutions of the initial solution (5-fold steps) were prepared, and 20 microliters of each were measured with a commercial photometer. To begin the measurement, 100 microliters of a 2% by weight solution of calcium hypochlorite were introduced into the sample to be analyzed. The results of a series of measurements are given in the following table:

| Amount of FITC (ng/ml) | Measured photons/sec |
| --- | --- |
| 20,000 | 18,101 |
| 4,000 | 8,485 |
| 800 | 2,748 |
| 160 | 735 |
| 32 | 394 |

The blank for the apparatus determined by making a measurement in the absence of FITC was, under these conditions, at most about 380 photons/sec. Accordingly, the detection threshhold for pure FITC was about 32 ng/ml.

In order to determine the detection threshhold for FITC bound to a protein, FITC was bound to goat immunoglobulin G by the method of B. T. Wood, S. H. Thomson and G. Goldstein, Journal of Immunology 95 (1964), p. 225. The optical density of the so prepared chemiluminescent conjugate was also measured at 495 nm with a photometer, and the amount of bound FITC was thereby determined. Then a dilution series of 10 dilutions was again prepared and the chemiluminescence of a 20 microliter sample of each dilution was determined. The results of the series of measurements are presented in the following table:

| Amount of FITC (ng/ml) | Measured photons/sec |
| --- | --- |
| 1,000 | 547 982 |
| 200 | 112 895 |
| 40 | 34 683 |
| 8 | 9 914 |

-continued

| Amount of FITC (ng/ml) | Measured photons/sec |
| --- | --- |
| 1.6 | 3 835 |
| 0.32 | 513 |
| 0.064 | 822 |
| 0.0128 | 378 |

The detection threshhold for the FITC-protein conjugate consequently is 0.064 ng/ml. From this it can be concluded that the FITC conjugate is extraordinarily well suited for detecting antigens, antibodies and their complexes in an immunological reaction by means of chemiluminescence.

EXAMPLE 2

Photon yield of methylene blue or thionine as markers

Methylene blue and thionine were prepared in volumes of 20 microliters each in the quantities shown in the following table. Methylene blue was activated by adding 100 microliters of an aqueous solution of chloramine T (16 mg/ml) and 100 microliters of a 10% by volume solution of hydrogen peroxide. Thionine was activated by adding 20 microliters of an aqueous solution of chloramine T (20 mg/ml) and 100 microliters of a 5% by volume solution of hydrogen peroxide. Over a reaction period of 30 seconds the excellent photon yields presented in the following table were measured:

| Marker | Amount | Photons/30 sec |
| --- | --- | --- |
| Methylene blue | 20 ng | 21,963 |
| " | 2 ng | 1,237 |
| " | 0.2 ng | 0 |
| Thionine | 2000 pg | 990,000 |
| " | 200 pg | 780,000 |
| " | 20 pg | 210,000 |
| " | 2 pg | 33,000 |
| " | 0.2 pg | 10,000 |

Note:
The blank value for thionine was 1700 photons.

The photon yield using thionine activated with $H_2O_2$/chloramine T was also measured, with the concentration of both components of the activator combination being varied. In this experiment, 2 pg of thionine in 20 microliters of distilled water were prepared. The measured results are presented in the following table. The blank for each measurement is indicated in parentheses.

| | Concentration of chloramine T | | | |
| --- | --- | --- | --- | --- |
| | 20 mg/ml | 40 mg/ml | 60 mg/ml | 80 mg/ml |
| 30% $H_2O_2$ | 15,100 (2,000) | 15,500 (4,300) | 21,000 (8,000) | 25,400 (12,000) |
| 20% $H_2O_2$ | 15,600 (1,950) | 23,300 (6,800) | 29,000 (8,300) | 36,000 (15,000) |
| 10% $H_2O_2$ | 44,000 (1,700) | 61,800 (7,800) | 65,000 (18,000) | 77,000 (26,000) |
| 5% $H_2O_2$ | 76,000 (1,600) | 103,000 (9,100) | 101,000 (24,000) | 121,000 (45,000) |

EXAMPLE 3

Detection of antibodies to bovine serum albumin (BSA) in rabbit serum.

BSA was adsorbed onto a flexible microtiter plate. To prepare this plate, 0.1 mg/ml of BSA was dissolved in a solution which was buffered at a pH of 9.6 with a sodium carbonate buffer. Into each well of the microtiter plate 100 microliters of the solution were pipetted. The plate was then incubated for 16 hours at 4° C. After aspirating the solution and washing the plate three times with a phosphate buffered salt solution having a pH of 7.4, which contained 1% of sorbimacrogol laurate (cf. Rompp's Chemilexikon, 7th Edition, 1967, Vol. 6, p. 3711, col. 1, under T. 20), a dilution series of rabbit serum was added to the wells and the plate was incubated for 90 minutes at 37° C. After aspirating the serum and again washing the plate three times, each well was incubated with an FITC-labeled anti-rabbit serum under the same conditions. After again washing the plate three times, the individual wells were cut out and the chemiluminescence was measured with a commercial photometer. In this case the chemiluminscence was stimulated by adding 100 microliters of $H_2O_2$ (30%) and 100 microliters of chloramine (79 mg/ml). The results of the measurement are shown in the single FIGURE of the drawings. The numerical values of the ordinate give the number of photons measured. The numerical values of the abscissa indicate the degree of dilution of the rabbit hyperimmune serum, while the blank is a value which was determined in a special way. In this procedure, the average value of the blank $\overline{X}$ was determined from several blank measurements, and to this value the product of $2.58 \times \delta$ was added, whereby the factor $\delta$ indicates the standard deviation. The FIGURE shows that the threshhold titer of the rabbit serum is about 1:32788. The same rabbit serum has a threshhold titer of 1:4096 in radioimmunoassay and 1:512 in ELISA.

Equivalent good results were obtained when the anti-rabbit serum was marked with methylene blue or thionine which was coupled using (N-ethyl-N'-(3-dimethylaminopropyl))carbodiimide hydrochloride.

Having now fully described the invention, it will be apparent to one of ordinary skill in the art that many changes and modifications can be made thereto without departing from the spirit or scope of the invention as set forth herein.

What is claimed as new and sought to be protected by Letters Patent of the United States is:

1. A process for qualitative and quantitative analysis of an immunological reagent selected from the group consisting of antigens, antibodies and antigen-antibody complexes comprising:
   (a) binding to said immunological reagent a chemiluminescent conjugate comprising an antibody, antigen, or binding protein capable of binding to said immunological reagent which is attached to a chemiluminescent marker selected from the group consisting of fluorescein, methylene blue, thionine and functionally equivalent derivatives of these markers,
   (b) contacting said bound chemiluminescent marker with an activator selected from the group consisting of mixtures of hydrogen peroxide and chloramine or functionally equivalent derivative of chloramine,
   (c) measuring the light emitted by said activated chemiluminescent marker.

2. The process of claim 1 wherein said activator is a mixture of hydrogen peroxide and chloramine T.

3. The process of claim 2 wherein said activator is a mixture of equal volumes of a 0.5 to 30% by volume aqueous solution of hydrogen peroxide and a 0.1 to 8% by weight solution of chloramine T.

4. The process of claim 1 or claim 2 wherein said antigen-antibody complex is prepared by a sandwich immunoassay.

5. The process of claim 1 or claim 2 wherein said contact is carried out in an aqueous medium.

6. The process of claim 5 wherein said chemiluminescent emission is measured in a basic aqueous medium.

7. The process of claim 1 or claim 2 wherein said functionally equivalent derivative of fluorescein is selected from the group consisting of fluorescein isothiocyanate and fluorescein isocyanate.

8. The process of claim 1 or claim 2 wherein said immunological reagent is selected from the group consisting of hepatitis B antigen and antibodies against herpesvirus or togavirus.

* * * * *